United States Patent [19]
Girten et al.

[11] Patent Number: 5,888,978
[45] Date of Patent: Mar. 30, 1999

[54] METHOD FOR REDUCING THE SEVERITY OF GASTRO-INTESTINAL DAMAGE

[75] Inventors: Beverly E. Girten; Paul Omholt, both of San Diego; Ronald R. Tuttle, Escondido, all of Calif.

[73] Assignee: Trega Biosciences, Inc., San Diego, Calif.

[21] Appl. No.: 527,252

[22] Filed: Sep. 12, 1995

[51] Int. Cl.$^6$ ............................. C07K 7/06; C07K 5/12; C07K 5/10; A61K 38/04
[52] U.S. Cl. .................. 514/16; 514/8; 514/17; 514/18; 514/9; 530/300; 530/317; 530/322; 530/329; 530/330
[58] Field of Search ................... 514/8, 16–18, 514/9; 530/300, 317, 322, 329, 330, 351; 424/85.1

[56] References Cited

U.S. PATENT DOCUMENTS 5,420,109  5/1995  Suto et al. .................... 514/8

OTHER PUBLICATIONS

Webster's II New Riverside University Dictionary, Riverside Publishing Co.:USA, p. 828, 1994.

Casini–Raggi et al., Anti–inflammatory effects of CGP 47969A, a novel inhibitor of proinflammatory cytokine synthesis, in rabbit immune colitis, Gastroenterology, 109: 821–818, Sep. 1995.

Radford–Smith et al., The role of cytokines in inflammatory bowel disease, Mediators of Inflammation, 3: 3–9, 1994.

Abou–Mohamed et al., "HP–228, a novel synthetic poeptide, inhibits the induction of nitric oxide synthase in vivo but no in vitro." *J. Pharmacol. Exp. Ther.,* 275(2):584–591 (Nov. 1995).

Perkins et al.,"Polymer delivery of the active isomer of misoprostol: a solution to the intestinal side effect problem." *J. of Pharm. and Experimental Therapeutics,* 269(1):151–156 (1994).

Perkins et al., "SC–46275: A potent, long–acting gastric antisecretory prostaglandin with low oral bioavailability in the dog." *J. of Pharm. and Experimental Therapeutics,* 259(3):1004–1007 (1991).

Sun et al., "Effects of a polysaccharide fraction from the roots of *bupleurum falcatum* L. on experimental gastric ulcer models in rats and mice." *J. Pharm. Pharmacol.,* 43:699–704 (1991).

McCafferty et al., "Indomethacin–induces gastric injury and leukocyte adherence in arthritic versus healthy rats." *Gastroenterology,* 109:1173–1180 (1995).

Andrews et al., "Effect of nonsteroidal anti–inflammatory drugs on LFA–1 and ICAM–1 expression in gastric mucosa." *Am. J. Physiol.,* 266 (4 Pt 1):G657–64 (1994).

Santucci et al., "Role of tumor necrosis factor α release and leukocyte margination in indomethacin–induced gastric injury in rats." *Gastroenterology,* 108:393–401 (1995).

Abstract of Wallace et al., "Nitric oxide–releasing non–steroidal anti–inflammatory drugs: a novel approach for reducing gastrointenstinal toxicity." *J. Gastorenterol Hepatol.,* 9(Suppl) 1:S40–4 (1994).

*Primary Examiner*—Lila Feisee
*Assistant Examiner*—Claire M. Kaufman
*Attorney, Agent, or Firm*—Campbell & Flores LLP

[57] ABSTRACT

The present invention provides methods for reducing the severity of GI damage in an individual by administering a cytokine regulatory agent to an individual that is susceptible to developing such damage.

24 Claims, No Drawings

METHOD FOR REDUCING THE SEVERITY OF GASTRO-INTESTINAL DAMAGE

BACKGROUND OF THE INVENTION

FIELD OF THE INVENTION

This invention relates generally to the field of molecular medicine and, more specifically, to the use of a cytokine regulatory agent to reduce the severity of gastro-intestinal damage in an individual.

BACKGROUND INFORMATION

Non-steroidal anti-inflammatory drugs (NSAID's) such as indomethacin (Indocin®) and ibuprofen (Advil®) are commonly prescribed for treating inflammation and pain. NSAID's are the treatment of choice to alleviate the chronic pain associated, for example, with arthritic diseases such as rheumatoid arthritis. However, NSAID's are known to have adverse side effects. In particular, patients being treated with NSAID's must be routinely monitored for signs of gastro-intestinal ulceration, which can arise suddenly and can be life threatening.

A role for prostaglandins in the inflammatory response that leads to the development of gastro-intestinal (GI) damage in a NSAID treated individual has led researchers to investigate the usefulness of prostaglandin analogs as a means for preventing GI damage. Some prostaglandin analogs such as misoprostol (Cytotec®) can reduce the severity of GI damage caused by administration of NSAID's.

Unfortunately, administration of prostaglandin analogs can produce unacceptable side effects in a treated individual. For example, these analogs can induce abdominal cramping leading to abortion in pregnant women and, therefore, are contraindicated for treating women of child-bearing age. Thus, a need exists to identify agents that can reduce the severity of GI damage in a subject without causing undesirable side effects. The present invention satisfies this need and provides related advantages as well.

SUMMARY OF THE INVENTION

The present invention provides a method of using a cytokine regulatory agent (CRA) to reduce the severity of gastro-intestinal (GI) damage in an individual susceptible to such damage. The invention provides, for example, a method of administering a CRA such as CRA-1 to an individual receiving a NSAID, wherein administration of the CRA reduces the severity of GI damage induced by the NSAID.

DETAILED DESCRIPTION OF THE INVENTION

The present invention provides a method of using a cytokine regulatory agent (CRA) to reduce the severity of GI damage in an individual susceptible to such damage. CRA's are known in the art and described, for example, in U.S. Pat. No. 5,420,109; issued May 30, 1995, which is incorporated herein by reference (CRA's previously were known as "cytokine restraining agents").

As disclosed herein, a CRA can reduce the severity of GI damage that can occur in an individual that is susceptible to such damage. In general, a CRA has the structure:

$X_1$-$X_2$-His-(D)Phe-Arg-(D)Trp-$X_3$, wherein $X_1$ is

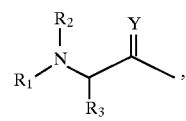

, H or $COCH_3$;

$X_2$ is

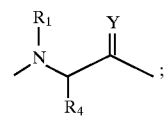

; and $X_3$ is

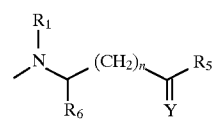

or $R_5$;

wherein Y is O, $H_2$ or S; $R_1$ is H, $COCH_3$, $C_2H_5$, $CH_2Ph$, COPh, COO—t—butyl, $COOCH_2Ph$, $CH_2CO$—(polyethylene glycol) or A; $R_2$ is H or $COCH_3$; $R_3$ is a linear alkyl group having 1 to 6 carbon atoms or a cyclic or branched alkyl group having 3 to 6 carbon atoms; $R_4$ is $(CH_2)_m$—$CONH_2$, $(CH_2)_m$—$CONHR_1$ or $(CH_2)_m$—CONHA; $R_5$ is OH, $OR_3$, $NH_2$, SH, $NHCH_3$, $NHCH_2Ph$ or A; and $R_6$ is H or $R_3$;

and wherein "Ph" is $C_6H_5$, "m" is 1, 2 or 3, "n" is 0, 1, 2 or 3, and "A" is a carbohydrate having the general formula:

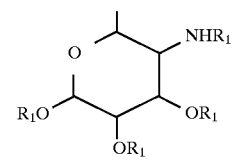

(U.S. Pat. No. 5,420,109; supra, 1995).

In addition, a CRA can have the structure:

$X_4$-$X_5$-(D)Phe-Arg-(D)Trp-$X_3$, wherein $X_4$ is

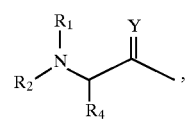

H, $COCH_3$ or absent $X_5$ is His, H or $COCH_3$; and

X₃ is

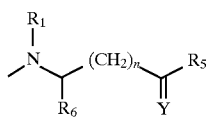

NH₂ or OH;

wherein Y is O, H₂ or S; R₁ is H, COCH₃, C₂H₅, CH₂Ph, COPh, COO—t—butyl, COOCH₂Ph, CH₂CO—(polyethylene glycol) or A; R₂ is H or COCH₃; R₃ is a linear alkyl group having 1 to 6 carbon atoms or a cyclic or branched alkyl group having 3 to 6 carbon atoms; R₄ is (CH₂)ₘ—CONH₂, (CH₂)ₘ—CONHR₁ or (CH₂)ₘ—CONHA; R₅ is OH, OR₃, NH₂, SH, NHCH₃, NHCH₂Ph or A; and R₆ is H or R₃;

and wherein "Ph" is C₆H₅, "m" is 1, 2 or 3, "n" is 0, 1, 2 or 3, and "A" is a carbohydrate having the general formula

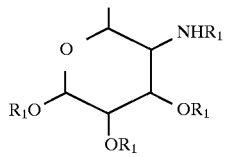

(see U.S. Pat. No. 5,420,109, supra, 1995, which also discloses methods for making a CRA).

In general, a CRA is a peptide or a peptide-like structure such as a peptidomimetic or a peptoid (see Ecker and Crooke, *Biotechnology* 13:351–360 (1995), and Blondelle et al., *Trends Anal. Chem.* 14:83–92 (1995), and the references cited therein, each of which is incorporated herein by reference). Amino acids are indicated herein by their commonly known three letter code, where "(D)" designates an amino acid having the "D" configuration, as compared to the naturally occurring (L)-amino acids; "Nle" is the three letter code for norleucine. Where no specific configuration is indicated, one skilled in the art would understand the amino acid to be an (L)-amino acid. In the CRA structures shown above, "Ph" indicates a "phenyl" group (C₆H₅). CRA peptides are written in the conventional manner, such that the amino terminus (N-terminus) is shown to the left and the carboxy terminus (C-terminus) is shown to the left.

One skilled in the art would know that the choice of amino acids or amino acid analogs incorporated into the peptide will depend, in part, on the specific physical, chemical or biological characteristics required of the CRA. Such characteristics are determined, for example, by the route by which the CRA is administered.

Selective modification of a reactive group in a peptide also can impart desirable characteristics to a CRA. For example, the N-terminus can be modified by acetylation or the C-terminus can be modified by amidation. Methods for modifying the N-terminus or C-terminus of a peptide are well known in the art (see, for example, in U.S. Pat. No. 5,420,109, supra, 1995). The choice of modifications made to the reactive groups present on the peptide is determined by a desirable characteristic required in the CRA. The CRA having the structure Ac-Nle-Gln-His-(D)Phe-Arg-(D)Trp-Gly-NH₂ (CRA-1) is an example of a CRA that is modified at both the N-terminus and C-terminus.

A cyclic peptide also can be an effective CRA. A cyclic peptide can be obtained by inducing the formation of a covalent bond between, for example, the amino group at the N-terminus of the peptide and the carboxyl group at the C-terminus. For example, the peptide, cyclo(His-(D)Phe-Arg-(D)Trp), can be produced by inducing the formation of a covalent bond between His and (D)Trp. Alternatively, a cyclic peptide can be obtained by forming a covalent bond between a terminal reactive group and a reactive amino acid side chain or between two reactive amino acid side chains. One skilled in the art would know that the choice of a particular cyclic peptide is determined by the reactive groups present on the peptide as well as the desired characteristic of the peptide. For example, cyclization of a CRA peptide can provide the CRA with increased stability in vivo.

As disclosed herein, administration of a CRA to an individual susceptible to developing GI damage can reduce the severity of such damage. It should be recognized that, although a CRA is referred to as a cytokine regulatory agent, no mechanism of action is proposed herein for the effectiveness of a CRA in reducing the severity of GI damage. Thus, a CRA may reduce the severity of GI damage by regulating cytokine activity or by some other mechanism that can be unrelated to cytokines.

The terms "gastro-intestinal damage" and "ulcer" are used interchangeably herein to mean a region of inflammation or denudation in one or more parts of the GI tract, including the stomach, small intestine or large intestine, or a junction between the parts of the GI tract, including the junction of the esophagus and stomach. Such damage is clinically relevant because it can develop suddenly, leading to abdominal pain and diarrhea and, if not quickly treated, can be fatal.

GI damage can be caused by various agents including, for example, drugs or chemicals that inflame or erode the mucosal lining of a portion of the GI tract. For example, GI damage can develop in an individual being treated with a non-steroidal anti-inflammatory drug (NSAID) such as indomethacin or ibuprofen. GI damage also can develop due to physical or psychological stress, which can increase the secretion of acids or proteolytic enzymes, or due to a bacterial infection, which can result in mucosal ulceration. In addition, GI damage can occur as a result of a chronic or hereditary disease such as ulcerative colitis or Crohn's disease.

As used herein, the term "individual susceptible to developing GI damage" means a mammalian subject, generally a human, that is at risk of developing GI damage as defined above. A person being treated with a NSAID, for example, to relieve the symptoms associated with an arthritic disease, is an example of such an individual, as is a person having a disease such as Crohn's disease.

As used herein, the term "reducing the severity of GI damage" is used in its broadest sense to mean a decrease in the extent of such damage or a decrease in a clinical sign or symptom associated with such damage. Administration of a CRA reduces the likelihood that an individual will get diarrhea or die following exposure to an NSAID (see Example I). Thus, a CRA is useful as a medicament for reducing the severity of GI damage in an individual susceptible to developing such damage. A reduction in the severity of GI damage can be determined by observing a decrease, for example, in abdominal pain or diarrhea, or by inspecting the mucosa of the GI tract using various medical procedures such as endoscopy.

As disclosed herein, administration of a CRA reduced the severity of GI damage in indomethacin treated rats. The effect of indomethacin administration on GI damage to rats is a well recognized model for studying the efficacy of agents that can affect GI damage (see, for example, Perkins et al., *J. Pharmacol. Expt. Ther.* 269:151–156 (1994)). In the model system used in the experiments described in Example I, the appearance of diarrhea and animal survival were determined following administration of indomethacin, alone, or with concurrent treatment using a cytokine regulatory agent.

A CRA can be administered to an individual as a pharmaceutical composition, which contains the CRA and a pharmaceutically acceptable carrier. Pharmaceutically acceptable carriers are well known in the art and include aqueous solutions such as water, physiologically buffered saline or other solvents or vehicles such as glycols, glycerol, oils such as olive oil or injectable organic esters.

A pharmaceutically acceptable carrier can contain physiologically acceptable compounds that act, for example, to stabilize the CRA or increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the CRA and on the particular physico-chemical characteristics of the specific CRA.

A CRA can be administered to an individual by various routes including, for example, orally or parenterally, such as intravenously, intramuscularly, subcutaneously, intraorbitally, intracapsularly, intraperitoneally, intrarectally intracisternally or by passive or facilitated absorption through the skin using, for example, a skin patch or transdermal iontophoresis, respectively. Furthermore, the composition can be administered by injection, intubation, orally or topically, the latter of which can be passive, for example, by direct application of an ointment or powder, or active, for example, using a nasal spray or inhalant. Preferably, the CRA is administered orally or by injection. A CRA also can be administered as a topical spray, in which case one component of the composition is an appropriate propellant. The pharmaceutical composition also can be incorporated, if desired, into liposomes, microspheres or other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

In order to reduce the severity of GI damage, the CRA must be administered in an effective dose, which is about 0.01 to 100 mg/kg body weight. The total effective dose can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a CRA required to obtain an effective dose in a subject depends on many factors including the age and general health of the subject as well as the route of administration and the number of treatments to be administered. In view of these factors, the skilled artisan would adjust the particular dose so as to obtain an effective dose for reducing the severity of GI damage.

The following examples are intended to illustrate but not limit the invention.

EXAMPLE I

USE OF A CRA TO REDUCE THE SEVERITY OF GI DAMAGE

This example demonstrates that administration of a CRA effectively reduces diarrhea and death due to GI damage.

The CRA, Ac-Nle-Gln-His-(D)Phe-Arg-(D)Trp-Gly-NH$_2$ (CRA-1), was prepared as described (U.S. Pat. No. 5,420, 109, supra, 1995). Adult male Harlan Sprague-Dawley rats (325–425 g) were divided into four groups (6 rats/group). Rats were weighed every morning and food was removed prior to receiving any treatment. Two groups of rats were pretreated by intraperitoneal (ip) injection of sterile saline, alone ("control"), and the remaining two groups were pretreated by ip injection of CRA-1 (100 μg/kg in saline). Pretreatment injections were administered between 8:00–9:00 am.

One hr following the pretreatment, one group of control rats was injected ip, on the side opposite the initial injection, with saline (Sal-control) and the other control group was injected with indomethacin (Ind-control; 10 mg/kg in saline, adjusted to pH 7.5–8.5 with NaOH). Similarly, the two groups of CRA-1 treated rats received either saline (Sal-CRA-1) or indomethacin (Ind-CRA-1). At 8 hr and 16 hr after the pretreatment, control rats and CRA-1 rats were administered saline or CRA-1, respectively. Food was returned to the rats after the 8 hr injection. This protocol was repeated for 7 days.

On day 4 of treatment, 5 of the 6 Ind-saline rats had diarrhea (83.3%). By day 7, 3 of the 6 Ind-saline rats had died and the 3 surviving rats had diarrhea. By day 8, 4 of the 6 Ind-saline rats had died (66.7% lethality). In contrast, none of the Ind-CRA-1 rats had diarrhea at day 4. By day 7, 1 of the 6 Ind-CRA-1 rats had died and 2 of the surviving 5 rats had diarrhea (40%). No additional deaths occurred in the Ind-CRA-1 treated rats by day 8 (83.3% survival; 5/6) and only 1 additional rat had diarrhea (60%; 3/5). These results demonstrate that a CRA can reduce the severity of GI damage induced by a NSAID.

Although the invention has been described with reference to the example provided above, it should be understood that various modifications can be made without departing from the spirit of the invention. Accordingly, the invention is limited only by the following claims.

We claim:

1. A method of reducing the severity of gastro-intestinal (GI) damage due to administration of a non-steroidal anti-inflammatory drug (NSAID) to an individual who is susceptible to developing such damage, comprising administering to the individual an effective dose of a cytokine regulatory agent (CRA) having the structure:

$X_1$-$X_2$-His-(D)Phe-Arg-(D)Trp-$X_3$, wherein:

$X_1$ is

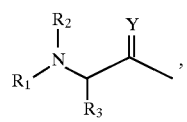

H or COCH$_3$;

$X_2$ is

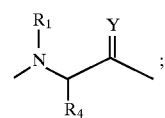

and $X_3$ is

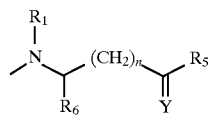

or $R_5$;
wherein Y is O, $H_2$ or S;
$R_1$ is H, $COCH_3$, $C_2H_5$, $CH_2Ph$, $COPh$, $COOCH_2Ph$, COO—t—butyl, $CH_2CO$—(polyethylene glycol) or A;
$R_2$ is H or $COCH_3$;
$R_3$ is a linear alkyl group having 1 to 6 carbon atoms or a cyclic or branched alkyl group having 3 to 6 carbon atoms;
$R_4$ is $(CH_2)_m$—$CONH_2$, $(CH_2)_m$—$CONHR_1$ or $(CH_2)_m$—CONHA;
$R_5$ is OH, $OR_3$, $NH_2$, SH, $NHCH_3$, $NHCH_2Ph$ or A; and
$R_6$ is H or $R_3$;
and wherein "Ph" is $C_6H_5$, "m" is 1, 2 or 3, "n" is 0, 1, 2 or 3, "A" is a carbohydrate having the general formula:

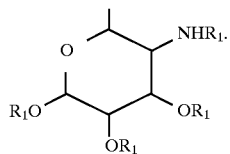

2. The method of claim 1, wherein the amino terminus of said CRA is modified by acetylation.

3. The method of claim 1, wherein the carboxyl terminus of said CRA is modified by amidation.

4. The method of claim 1, wherein $R_1$ is selected from the group consisting of H, $C_2H_5$ and $CH_2Ph$.

5. The method of claim 1, wherein $R_1$ and $R_2$ are each H.

6. The method of claim 1, wherein $X_1$ is selected from the group consisting of norleucine, norvaline, leucine or isoleucine.

7. The method of claim 1, wherein $R_5$ is covalently bound to $X_1$, said covalent bond forming a cyclic peptide.

8. The method of claim 1, wherein said CRA has the structure:

Nle-Gln-His-(D)Phe-Arg-(D)Trp-Gly-$NH_2$.

9. The method of claim 8, wherein the amino terminus of said CRA is acetylated.

10. A method of reducing the severity of GI damage in an individual susceptible to developing such damage, comprising administering to the individual an effective dose of a CRA having the structure: Ac-(cyclohexyl)Gly-Gln-His-(D)Phe-Arg-Trp-Gly-$NH_2$.

11. A method of reducing the severity of GI damage due to administration of a non-steroidal anti-inflammatory drug (NSAID) to an individual who is susceptible to developing such damage, comprising administering to the individual an effective dose of a CRA having the structure:

$X_4$-$X_5$-(D)Phe-Arg-(D)Trp-$X_3$, wherein:

$X_4$ is

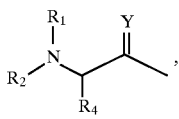

H, $COCH_3$ or absent;
$X_5$ is His, H or $COCH_3$; and
$X_3$ is

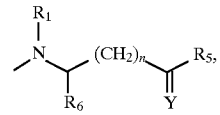

or OH;
wherein Y is O, $H_2$ or S;
$R_1$ is H, $COCH_3$, $C_2H_5$, $CH_2Ph$, $COPh$, $COOCH_2Ph$, COO—t—butyl, $CH_2CO$—(polyethylene glycol) or A;
$R_2$ is H or $COCH_3$;
$R_3$ is a linear alkyl group having 1 to 6 carbon atoms or a cyclic or branched alkyl group having 3 to 6 carbon atoms;
$R_4$ is $(CH_2)_m$—$CONH_2$, $(CH_2)_m$—$CONHR_1$ or $(CH_2)_m$—CONHA;
$R_5$ is OH, $OR_3$, $NH_2$, SH, $NHCH_3$, $NHCH_2Ph$ or A; and
$R_6$ is H or $R_3$;
and wherein "Ph" is $C_6H_5$, "m" is 1, 2 or 3, "n" is 0, 1, 2 or 3, and "A" is a carbohydrate having the general formula:

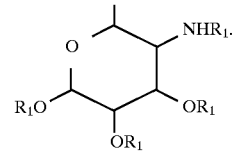

12. The method of claim 11, wherein the amino terminus of said CRA is modified by acetylation.

13. The method of claim 11, wherein the carboxyl terminus of said CRA is modified by amidation.

14. The method of claim 11, wherein $R_1$ is selected from the group consisting of H, $C_2H_5$ and $CH_2Ph$.

15. The method of claim 11, wherein $R_1$ and $R_2$ are each H.

16. The method of claim 11, wherein $R_5$ is covalently bound to $X_4$, said covalent bond forming a cyclic peptide.

17. The method of claim 11, wherein said CRA has the structure: His-(D)Phe-Arg-(D)-Trp-Gly.

18. The method of claim 17, wherein the carboxyl terminus of said CRA is modified by amidation.

19. The method of claim 17, wherein the amino terminus of said CRA is acetylated.

20. The method of claim 11, wherein said CRA has the structure: His-(D)Phe-Arg-(D)Trp.

21. The method of claim 20, wherein the amino terminus of said CRA is modified by acetylation.

22. The method of claim 20, wherein the carboxyl terminus of said CRA is modified by amidation.

23. A method of reducing the severity of GI damage in an individual susceptible to developing such damage, comprising administering to the individual an effective dose of a CRA having the structure: cyclo(His-(D)Phe-Arg-(D)Trp).

24. A method of reducing the severity of GI damage due to administration of a non-steroidal anti-inflammatory drug (NSAID) to an individual who is susceptible to developing such damage, comprising administering to the individual an effective dose of a CRA having the structure: Ac-His-(D)Phe-Arg-(D)Trp-(CH$_2$NHAc)-Gly-NH$_2$.

UNITED STATES PATENT AND TRADEMARK OFFICE
CERTIFICATE OF CORRECTION

PATENT NO.   : 5,888,978
DATED        : March 30, 1999
INVENTOR(S)  : Girten et al.

It is certified that error appears in the above-identified patent and that said Letters Patent is hereby corrected as shown below:

Column 7,
Line 25, after "3," please insert -- and --.
Line 59, please delete "Phe-Arg-Trp-Gly-NH$_2$." and replace with
-- Phe-Arg-(D)Trp-Gly-NH$_2$. --.

Signed and Sealed this

Thirteenth Day of August, 2002

Attest:

JAMES E. ROGAN
Attesting Officer     Director of the United States Patent and Trademark Office

UNITED STATES PATENT AND TRADEMARK OFFICE
CERTIFICATE OF CORRECTION

PATENT NO.   : 5,888,978
DATED        : March 30, 1999
INVENTOR(S)  : Girten et al.

It is certified that error appears in the above-identified patent and that said Letters Patent is hereby corrected as shown below:

Column 8,
Line 19, before "or OH;" insert -- $NH_2$ --.

Signed and Sealed this

Thirteenth Day of July, 2004

JON W. DUDAS
*Acting Director of the United States Patent and Trademark Office*